(12) United States Patent
Cortiñas Villazón et al.

(10) Patent No.: US 11,986,195 B2
(45) Date of Patent: May 21, 2024

(54) DEVICE AND A THROMBECTOMY APPARATUS FOR EXTRACTION OF THROMBUS FROM A BLOOD VESSEL

(71) Applicant: ANACONDA BIOMED, SL, Sant Quirze del Vallès (ES)

(72) Inventors: Ignacio Cortiñas Villazón, Barcelona (ES); Ane Lizarazu González, Barcelona (ES); Ofir Arad Hadar, Sant Cugat del Vallès (ES); Iñaki Galve Murillo, Barcelona (ES)

(73) Assignee: Anaconda Biomed, S.L., Sant Quirze del Vallès (ES)

( * ) Notice: Subject to any disclaimer, the term of this patent is extended or adjusted under 35 U.S.C. 154(b) by 0 days.

(21) Appl. No.: 17/274,973

(22) PCT Filed: Oct. 16, 2019

(86) PCT No.: PCT/EP2019/078088
§ 371 (c)(1),
(2) Date: Mar. 10, 2021

(87) PCT Pub. No.: WO2020/079082
PCT Pub. Date: Apr. 23, 2020

(65) Prior Publication Data
US 2021/0393280 A1 Dec. 23, 2021

(30) Foreign Application Priority Data
Oct. 16, 2018 (EP) ..................... 18382736

(51) Int. Cl.
*A61B 17/221* (2006.01)
*A61L 31/02* (2006.01)
(Continued)

(52) U.S. Cl.
CPC .......... *A61B 17/221* (2013.01); *A61L 31/022* (2013.01); *A61L 31/10* (2013.01);
(Continued)

(58) Field of Classification Search
CPC .......... A61B 17/12022; A61B 17/1204; A61B 17/12109; A61B 17/2131;
(Continued)

(56) References Cited

U.S. PATENT DOCUMENTS

| | | | |
|---|---|---|---|
| 4,921,478 A | 5/1990 | Solano et al. | |
| 5,011,488 A | 4/1991 | Ginsburg | |

(Continued)

FOREIGN PATENT DOCUMENTS

| | | |
|---|---|---|
| CN | 102973332 A | 3/2013 |
| CN | 104159525 A | 11/2014 |

(Continued)

OTHER PUBLICATIONS

Berkhemer et al.; A randomized trial of intraarterial treatment for acute ischemic stroke; New England Journal of Medicine; 372; pp. 11-20; Jan. 1, 2015.

(Continued)

*Primary Examiner* — Kankindi Rwego
(74) *Attorney, Agent, or Firm* — Shay Glenn LLP (57) ABSTRACT

A device, a thrombectomy apparatus and a method for extraction of thrombus from a blood vessel are disclosed. The device comprises a segment changing its shape from a retracted position in a compressed state to an extended and expanded position. The segment is formed by a mesh of at least two sets of helicoidal filaments turning respectively in opposite directions and being intertwined. The mesh comprises two distinct tubular sections. The mesh of the first section has helicoidal filaments with a braiding angle providing radial forces higher than in the second section, thus (Continued)

the first section becomes appositioned against the inner wall of the blood vessel. The second section comprises two sub-sections. The first sub-section has a conical shape and comprises a braiding angle changing at its proximal and distal ends to provide radial strength to maintain the conical shape and to stop a proximal blood flow during the removal of the thrombus.

14 Claims, 4 Drawing Sheets

(51) Int. Cl.
   *A61L 31/10* (2006.01)
   *A61B 17/22* (2006.01)
(52) U.S. Cl.
   CPC .............. *A61B 2017/22079* (2013.01); *A61B 2017/2212* (2013.01)
(58) Field of Classification Search
   CPC ........ A61B 17/12172; A61B 17/12136; A61B 17/22031; A61B 17/22032; A61B 17/221; A61B 17/02; A61B 17/0206; A61B 17/0218; A61B 17/0231; A61B 17/0281; A61B 17/0293; A61B 2017/0057; A61B 2017/2212; A61B 2017/2215; A61B 2017/2217; A61B 2017/22051; A61B 2017/0212; A61B 2017/0225; A61B 2017/0237; A61B 2017/0243; A61B 2017/0256; A61B 2017/0262; A61B 2017/0268; A61B 2017/0275; A61B 2017/0287; A61B 2017/22034; A61B 2017/22035; A61B 2017/22079; A61L 31/022; A61L 31/10
   USPC ....... 606/108, 127, 159, 191, 192, 194, 200; 604/19, 48, 96.01, 97.01
   See application file for complete search history.

(56) References Cited

U.S. PATENT DOCUMENTS

| | | | |
|---|---|---|---|
| 5,102,415 A | 4/1992 | Guenther et al. | |
| 5,190,561 A | 3/1993 | Graber | |
| 5,605,530 A | 2/1997 | Fishell et al. | |
| 5,769,871 A | 6/1998 | Mers Kelly et al. | |
| 5,908,435 A | 6/1999 | Samuels | |
| 5,971,938 A | 10/1999 | Hart et al. | |
| 6,159,230 A | 12/2000 | Samuels | |
| 6,190,303 B1 | 2/2001 | Glenn et al. | |
| 6,402,771 B1 | 6/2002 | Palmer et al. | |
| 6,663,650 B2 | 12/2003 | Sepetka et al. | |
| 6,695,858 B1 | 2/2004 | Dubrul et al. | |
| 6,752,819 B1 | 6/2004 | Brady et al. | |
| 7,001,425 B2* | 2/2006 | McCullagh | D04C 1/06 623/1.53 |
| 7,004,954 B1 | 2/2006 | Voss et al. | |
| 7,108,677 B2 | 9/2006 | Courtney et al. | |
| 7,578,830 B2 | 8/2009 | Kusleika et al. | |
| 7,686,825 B2 | 3/2010 | Hauser et al. | |
| 8,679,142 B2 | 3/2014 | Slee et al. | |
| 8,758,364 B2 | 6/2014 | Eckhouse et al. | |
| 8,784,441 B2 | 7/2014 | Rosenbluth et al. | |
| 8,858,497 B2 | 10/2014 | Di Palma et al. | |
| 8,864,792 B2 | 10/2014 | Eckhouse et al. | |
| 8,940,003 B2 | 1/2015 | Slee et al. | |
| 9,005,237 B2 | 4/2015 | Eckhouse et al. | |
| 9,034,008 B2 | 5/2015 | Eckhouse et al. | |
| 9,186,487 B2 | 11/2015 | Dubrul et al. | |
| 9,463,035 B1 | 10/2016 | Greenhalgh et al. | |
| 9,561,121 B2 | 2/2017 | Sudin et al. | |
| 9,585,741 B2 | 3/2017 | Ma | |
| 9,844,381 B2 | 12/2017 | Eckhouse et al. | |
| 9,861,783 B2 | 1/2018 | Garrison et al. | |
| 10,285,720 B2 | 5/2019 | Gilvarry et al. | |
| 10,426,644 B2 | 10/2019 | Shrivastava et al. | |
| 10,434,605 B2 | 10/2019 | Feth et al. | |
| 11,013,523 B2 | 5/2021 | Jacobi et al. | |
| 2004/0024416 A1* | 2/2004 | Yodfat | A61F 2/90 623/1.53 |
| 2004/0073243 A1 | 4/2004 | Sepetka et al. | |
| 2004/0098099 A1 | 5/2004 | McCullagh et al. | |
| 2004/0143317 A1* | 7/2004 | Stinson | A61L 31/022 623/1.15 |
| 2004/0243102 A1 | 12/2004 | Berg et al. | |
| 2004/0260333 A1* | 12/2004 | Dubrul | A61M 29/02 606/200 |
| 2005/0090857 A1* | 4/2005 | Kusleika | A61F 2/013 606/200 |
| 2006/0058838 A1 | 3/2006 | Bose et al. | |
| 2006/0064073 A1 | 3/2006 | Schonholz et al. | |
| 2006/0155305 A1* | 7/2006 | Freudenthal | A61B 17/221 606/114 |
| 2006/0293744 A1 | 12/2006 | Peckham et al. | |
| 2007/0213765 A1 | 9/2007 | Adams et al. | |
| 2007/0276332 A1 | 11/2007 | Bierman | |
| 2009/0163846 A1 | 6/2009 | Aklog et al. | |
| 2009/0198269 A1 | 8/2009 | Hannes et al. | |
| 2010/0004607 A1 | 1/2010 | Wilson et al. | |
| 2010/0030256 A1 | 2/2010 | Dubrul et al. | |
| 2010/0222864 A1 | 9/2010 | Rivelli et al. | |
| 2011/0160763 A1 | 6/2011 | Ferrera et al. | |
| 2011/0213297 A1 | 9/2011 | Aklog et al. | |
| 2012/0041449 A1* | 2/2012 | Eckhouse | A61B 17/221 606/127 |
| 2012/0059309 A1 | 3/2012 | Di Palma et al. | |
| 2012/0065660 A1 | 3/2012 | Ferrera et al. | |
| 2012/0083868 A1 | 4/2012 | Shrivastava et al. | |
| 2012/0114017 A1 | 5/2012 | Bang et al. | |
| 2012/0179181 A1 | 7/2012 | Straub et al. | |
| 2013/0261638 A1* | 10/2013 | Diamant | A61M 1/0023 606/113 |
| 2013/0325055 A1 | 12/2013 | Eckhouse et al. | |
| 2013/0325056 A1 | 12/2013 | Eckhouse et al. | |
| 2014/0052161 A1 | 2/2014 | Cully et al. | |
| 2014/0074144 A1 | 3/2014 | Shrivastava et al. | |
| 2014/0155908 A1 | 6/2014 | Rosenbluth et al. | |
| 2014/0243885 A1 | 8/2014 | Eckhouse et al. | |
| 2014/0277015 A1 | 9/2014 | Stinis | |
| 2015/0112376 A1 | 4/2015 | Molaei et al. | |
| 2015/0164666 A1 | 6/2015 | Johnson et al. | |
| 2015/0231360 A1 | 8/2015 | Watanabe et al. | |
| 2015/0327866 A1* | 11/2015 | Eckhouse | A61F 2/844 623/1.15 |
| 2015/0359547 A1 | 12/2015 | Vale et al. | |
| 2016/0081704 A1 | 3/2016 | Jeon et al. | |
| 2016/0256255 A9 | 9/2016 | Ma | |
| 2017/0065299 A1* | 3/2017 | Gillespie | A61F 2/962 |
| 2017/0105743 A1* | 4/2017 | Vale | A61B 17/22032 |
| 2017/0119408 A1 | 5/2017 | Ma | |
| 2017/0119409 A1 | 5/2017 | Ma | |
| 2017/0215900 A1* | 8/2017 | Lowinger | A61B 17/221 |
| 2017/0215902 A1 | 8/2017 | Leynov et al. | |
| 2017/0239444 A1 | 8/2017 | Parker | |
| 2017/0303949 A1* | 10/2017 | Ribo Jacobi | A61B 17/12109 |
| 2017/0333060 A1* | 11/2017 | Panian | A61M 25/0105 |
| 2018/0028209 A1 | 2/2018 | Sudin et al. | |
| 2018/0064454 A1 | 3/2018 | Losordo et al. | |
| 2018/0126132 A1 | 5/2018 | Heilman et al. | |
| 2018/0132876 A1 | 5/2018 | Zaidat | |
| 2018/0206862 A1 | 7/2018 | Long | |
| 2018/0318062 A1 | 11/2018 | Sudin et al. | |
| 2018/0353196 A1 | 12/2018 | Epstein et al. | |
| 2018/0361114 A1 | 12/2018 | Chou et al. | |
| 2019/0110805 A1 | 4/2019 | Ulm, III | |
| 2019/0167284 A1 | 6/2019 | Friedman et al. | |
| 2019/0167287 A1 | 6/2019 | Vale et al. | |
| 2019/0216476 A1 | 7/2019 | Barry et al. | |
| 2019/0269425 A1 | 9/2019 | Sudin et al. | |
| 2019/0269491 A1 | 9/2019 | Jalgaonkar et al. | |

(56) References Cited

U.S. PATENT DOCUMENTS

| | | |
|---|---|---|
| 2019/0274810 A1 | 9/2019 | Phouasalit et al. |
| 2019/0298396 A1 | 10/2019 | Gamba et al. |
| 2019/0307471 A1 | 10/2019 | Friedman et al. |
| 2019/0336727 A1 | 11/2019 | Yang et al. |
| 2020/0000613 A1 | 1/2020 | Shrivastava et al. |
| 2020/0008822 A1 | 1/2020 | Eckhouse et al. |
| 2020/0085444 A1 | 3/2020 | Vale et al. |
| 2020/0205838 A1 | 7/2020 | Walzman |
| 2020/0281612 A1 | 9/2020 | Kelly et al. |
| 2021/0000582 A1 | 1/2021 | Chomas et al. |
| 2021/0059695 A1* | 3/2021 | Harari .................. A61B 17/221 |
| 2021/0068852 A1 | 3/2021 | Spence |
| 2021/0077134 A1 | 3/2021 | Vale et al. |
| 2022/0117614 A1 | 4/2022 | Salmon et al. |
| 2023/0127145 A1 | 4/2023 | Arad Hadar et al. |

FOREIGN PATENT DOCUMENTS

| | | |
|---|---|---|
| CN | 107198554 B | 2/2020 |
| EP | 2662109 A1 | 11/2013 |
| ES | 2341978 T3 | 6/2010 |
| ES | 2381099 T3 | 5/2012 |
| GB | 2498349 A | 7/2013 |
| JP | 2005500138 A | 1/2005 |
| WO | WO99/45835 A2 | 9/1999 |
| WO | WO02/087677 A2 | 11/2002 |
| WO | WO2004/002564 A1 | 1/2004 |
| WO | WO2005/027751 A1 | 3/2005 |
| WO | WO2008/124567 A1 | 10/2008 |
| WO | WO2008/157202 A1 | 12/2008 |
| WO | WO2009/014723 A1 | 1/2009 |
| WO | WO2011/068924 A1 | 6/2011 |
| WO | WO2011/082319 A1 | 7/2011 |
| WO | WO2012/106657 A2 | 8/2012 |
| WO | WO2012/156924 A1 | 11/2012 |
| WO | WO2012/158269 A1 | 11/2012 |
| WO | WO2013/008233 A1 | 1/2013 |
| WO | WO2013/152327 A1 | 10/2013 |
| WO | WO2014/008460 A2 | 1/2014 |
| WO | WO2014/087245 A2 | 6/2014 |
| WO | WO2014/127389 A2 | 8/2014 |
| WO | WO2014/204860 A1 | 12/2014 |
| WO | WO2015/006782 A1 | 1/2015 |
| WO | WO2015/189354 A1 | 12/2015 |
| WO | WO2016/113047 A1 | 7/2016 |
| WO | WO2017/072663 A1 | 5/2017 |
| WO | WO2017/074290 A1 | 5/2017 |
| WO | WO2017/075544 A1 | 5/2017 |
| WO | WO2018/080590 A1 | 5/2018 |
| WO | WO2018/160966 A1 | 9/2018 |
| WO | WO2019/064306 A1 | 4/2019 |
| WO | WO2019/178131 A1 | 9/2019 |
| WO | WO2020/021333 A2 | 1/2020 |
| WO | WO2020/079082 A1 | 4/2020 |
| WO | WO2020/099386 A1 | 5/2020 |
| WO | WO2021/016213 A1 | 1/2021 |

OTHER PUBLICATIONS

Ceretrieve; 3 pages; retrieved from the internet (http://trendlines.com/portfolio/ceretrieve/) on Sep. 13, 2018.

Arad Hadar; U.S. Appl. No. 17/235,764 entitled "Thrombectomy device, system and method for extraction of vascular thrombi from a blood vessel," filed Apr. 20, 2021.

Duffy et al.; Novel methodology to replicate clot analogs with diverse composition in acute ischemic stroke; Journal of neurointerventional surgery; 9(5); pp. 486-491; May 1, 2017.

Fennell et al.; What to do about fibrin rich "tough clots"? Comparing the Solitaire stent retriever with a novel geometric clot extractor in an in vitro stroke model; Journal of neurointerventional surgery; 10(9); pp. 907-910; Sep. 1, 2018.

Mokin et al.; Stent retriever thrombectomy with the Cover accessory device versus proximal protection with a balloon guide catheter: in vitro stroke model comparison; Journal of neurointerventional surgery; 8(4); pp. 413-417; Apr. 1, 2016.

Arad Hadar et al.; U.S. Appl. No. 17/291,696 entitled "A thrombectomy system and methods of extracting a thrombus from a thrombus site in a blood vessel of a patient," filed May 6, 2021.

Ros Fàbrega et al.; U.S. Appl. No. 17/415,866 entitled "Loading device for loading a medical device into a catheter," filed Jun. 18, 2021.

Bouthillier et al.; Segments of the internal carotid artery: a new classification; Neurosurgery; 38(3); pp. 425-433; Mar. 1, 1996.

Rios Garriga et al.; U.S. Appl. No. 17/621,717 entitled "Delivery catheter device and system for accessing the intracranial vasculature," filed Dec. 22, 2021.

Castano et al.; Unwanted detachment of the Solitaire device during mechanical thrombectomy in acute ischemic stroke; Journal of neurointerventional surgery; 8(12); pp. 1226-1230; Dec. 1, 2016.

Penumbra Inc.; Recalls 3D revascularization device due to wire material that may break or separate during use; FDA Recall; retrieved from the internet (http://web.archive.org/web/20200813123505/https:/www.fda.gov/medical-devices/medical-device-recalls/penumbra-inc-recalis-3d-revascularization-device-due-wire-material-may-break-or-separate-during-use).

Garcia-Sabido et al.; U.S. Appl. No. 18/040,492 entitled "A clot mobilizer device for extraction of an occlusion from a blood vessel," filed Feb. 3, 2023.

Garcia-Sabido et al.; U.S. Appl. No. 18/040,495 entitled "An elongated device with an improved attachment of its elements," filed Feb. 3, 2023.

* cited by examiner

DEVICE AND A THROMBECTOMY APPARATUS FOR EXTRACTION OF THROMBUS FROM A BLOOD VESSEL

TECHNICAL FIELD

The present invention is directed, in general, to the field of medical devices. In particular, the invention relates to a device conceived for extraction of thrombus from a blood vessel and to a thrombectomy apparatus that includes said device. The invention also provides a method for extraction of thrombus from a blood vessel.

BACKGROUND OF THE INVENTION

The extraction of thrombus from a blood vessel has to solve the problem of thrombus fragmentation at the moment of the extraction with the risk of the dispersion of fragments of the thrombus through the blood vessel.

WO 2012156924-A1 discloses an apparatus for aspirating blood from a blood vessel through a catheter located in the blood vessel comprising an expandable member including a flow tube having at a distal end a flow blocker and a flow blocker control activating lines. Expansion support frame of flow blocker comprises a plurality of prestressed fingers that extend from a collar of and expandable pre-stressed rib cage.

WO 2016113047-A1, of the same applicant of present invention, discloses a thrombectomy apparatus comprising a delivery catheter, a dilator catheter and a funnel, defining a distal end and a proximal end. The funnel is positionable in a retracted position and in an extended position and comprises a covering. The diameter of the distal end of the funnel is greater in the extended position than in the retracted position. It permits an aspiration from a very close proximity to the thrombus and with a large mouth, allowing occlusion of the artery, stopping the flow, and aspirating the entire thrombus without fragmenting it.

US 20040098099-A1 relates to braided stents and stent-grafts having segments of different strength and rigidity along the length, and/or different diameters of varying or constant strength and rigidity along the length. Unlike the present invention, the braided stent of this US patent application comprises a distal end with a broader region delimited by a ring of sawtooth filament not suitable to capture a thrombus. Moreover, the braided stent further comprises a transition region (the central region 130) having a lower mesh density than the distal and proximal ends and a proximal end of the braided stent (i.e. narrow region 110) having greater flexibility than the distal end.

WO 2014087245-A2 discloses a treatment device and method for treatment. The treatment device can include a shaft, an expandable member, a first elongated control member and a second elongated control member. The expandable member can further include at least a first controllable portion and a second controllable portion, where the expandable member, including the first controllable portion and the second controllable portion, is configured to transition between at least a partially retracted configuration and an expanded configuration under control of at least the first elongated control member. Unlike the present invention, in the treatment device of this international patent application the variation of the girth and the filament density is controlled by said elongated control members, i.e. by external member, not by the mesh itself by means of having a particular braiding angle.

WO 2005027751-A1 discloses a thrombus/embolus collecting device, comprising a body part freely radially contracted and enlarged and normally radially enlarged in a cylindrical shape, a tail part formed continuously with the body part, freely radially contracted and enlarged, and normally radially enlarged in a tapered shape, a stent formed continuously with the tail part and formed of a strut part, and a bag-like (conical-shaped) filter formed of an opening part and a body part. The body part and the tail part of the stent are formed in a braided cord structure by spirally twisting one or a plurality of wires, the bag-like filter is inserted into the body part of the stent, and the opening part of the bag-like filter is engaged with the tip of the body part of the stent by an engagement means.

Apparatus or stents known to the inventors are not designed to have specific distribution of radial forces along their different portions/sections thus they cannot uniformly adapt its surface to be appositioned against the inner wall of a blood vessel to facilitate the reception and retention of a thrombus. Alternative devices and methods are therefore needed for extraction of thrombus from a blood vessel.

DESCRIPTION OF THE INVENTION

To that end, present invention proposes according to a first aspect a device for extraction of thrombus, of different sizes, shapes and dimensions, from a blood vessel. The proposed device, as the known solutions in the field, comprises a segment defining a distal end and a proximal end and is configured to adapt at least its shape to a surrounding blood vessel from a retracted position in a compressed state (in the delivery configuration), particularly inside a carrier, for example a delivery catheter, to an extended and expanded position (also referred in this description as "in a deployment configuration"), to be appositioned against the inner wall of a blood vessel to receive and retain a thrombus.

The proposed device, which is self-expandable, is formed by a mesh of at least two sets, equals or different, of helicoidal filaments (or wires) turning respectively in opposite directions and being intertwined. Likewise, the mesh comprises a first tubular section, particularly of a uniform diameter, and a second tubular section. The second section is comprised of a first sub-section having a shape with a progressive reduction of diameter, with a shape configured to open and create a space for the thrombus, and a second sub-section of a tubular uniform diameter configured to provide a connection to a catheter or to a hypotube (with appropriate connectors at the proximal end).

Unlike the known proposals in the field, the mesh of the first section has helicoidal filaments with a braiding angle ($\beta$) configured to provide radial forces, i.e. pressure, higher than in the second section (without needing additional control members as in the device taught by WO 2014087245-A2). Consequently, the first section becomes better appositioned, or overlapped, against the inner wall of the blood vessel.

Moreover, in the proposed device, the first sub-section has a conical shape (or funnel shape) and comprises a braiding angle (a) that changes at its proximal and distal ends to provide radial strength to maintain the conical shape and to stop a proximal blood flow during the removal of the thrombus. The term "stop a proximal blood flow" means blocking or reducing partially or substantially totally the blood flow during the intervention.

In an embodiment, the first section, i.e. the portion closer to said distal end, comprises closed loops at the distal end configured to act as a spring, such that the radial forces in first and second end portions (or extremes) of the first section are higher than in an intermediate portion of this first section. Moreover, because of the inclusion of the closed loops the expansion of the device (once it comes out of the carrier) is facilitated. Thus, the radial forces are increased. The cited loops also provide a smooth end to the device thus reducing the possible vessel damage and improving navigability conditions of the device within the blood vessel. Moreover, the cited loops reduce the possibility of entanglement with other devices, that at the same time, reduce the risk of damage of the blood vessel. Other options for increasing the radial forces are by having a single thread mesh in the first section, or by the first section having some weld spot, or by the density, composition or diameter of the mesh being higher.

The straight shape of the first section of the proposed device creates a space which will accommodate the thrombus once it has been aspirated. The first section is adaptable to the vessel geometry and its outer surface overlaps the inner wall of the blood vessel.

The proposed device can be produced in different sizes. In an embodiment, the first section is longer than the second section. In an embodiment, the first section comprises a length ranging between 4 and 40 millimeters and an outer diameter ranging between 3.5 and 6 millimeters, and the second sub-section comprises a length ranging between 1 and 10 millimeters and an outer diameter ranging between 1 and 2 millimeters. Moreover, the braiding angle (a) of the first sub-section is comprised between 15 and 45 degrees with regard to a longitudinal axis of the device. This angle favors having more radial force thereby stopping the flow, but at the same time that there is a seal of the blood vessel it also has to allow the device to be compressed.

In another embodiment, the proposed the device further comprises a coating, hydrophilic or hydrophobic. In an embodiment, the coating is a non-permeable coating. The coating can be disposed over the first section only or over the first and second sections. In this latter case, a portion of the second section besides the proximal end is preserved uncoated. The coating in an embodiment comprises a polymer such as silicone or polyurethane, among others. In an embodiment, the coating thickness is in the range between 5 and 25 µm, particularly 15 µm.

Moreover, the coating may comprise holes thus collapse of the device is avoided. Another option to avoid the collapse of the device is by the threads of the mesh having different diameter.

The helicoidal filaments of the mesh can be made of a metal, a metal alloy or a composite including, among others, Nitinol or Nitinol/Platinum, or also Niti #1-DFT$^R$ (Drawn Filled Tube), with a percentage of Platinum from 10% to 40%; in particular with 20% Platinum (Niti #1-DFT$^R$-20% Pt).

The helicoidal filaments, in an embodiment comprise a number ranging between 12 and 48 filaments, and particularly between 24 and 48 filaments. In particular, the number of filaments is 12, 18, 24 or 48; more particularly the number of filaments is 24. In this case, the filaments have a cross section comprised in a range between 40 and 60 µm, and particularly 50 µm, and the braiding angle (13) of the filaments with regard to the longitudinal axis of the device is comprised between 50 and 65 degrees for the first section, and between 15 and 50 for the second sub-section.

The device may also include or have attached thereto one or more sensors to provide information thereof. For example, a lighting sensor or sensors providing information of whether the device is in the retracted position within the carrier or in the extended and expanded position. The sensor(s) can alternatively, or additionally, provide information on whether the device is well extended and expanded, on whether the thrombus is in or out, about the composition of the thrombus, or about the position of the funnel in relation to the blood vessel. Alternatively, the sensor(s) may include a piezoelectric sensor providing information about the radial forces in each of the different sections or subsections of the device. Alternatively, the sensor(s) may provide information to distinguish between clot obstruction and intracranial atherosclerotic disease.

Advantageously, the proposed device can also comprise at least one radiopaque marker at its distal end and/or other strategic point(s) of the mesh which allow a physician to know the precise location of the device while using fluoroscopy.

Another aspect of the invention is related to a thrombectomy apparatus including the device of the first aspect of the invention, and particular embodiments thereof.

Yet another aspect of the invention provides a method of extracting a thrombus from a thrombus site in a blood vessel of a patient. In some embodiments, the method includes the steps of advancing a thrombus extraction device through a delivery catheter in a delivery configuration to a thrombus site within a blood vessel, the thrombus extraction device including a mesh of at least first and second sets of oppositely wound and intertwined helicoidal filaments having a first section at a distal end and a second section extending proximally from a proximal end of the first section, the first set of helicoidal filaments forming a distally facing first angle with the second set of helicoidal filaments in the delivery configuration; expanding the first section of the thrombus extraction device with a first outward radial force into a deployment configuration in apposition with an inner wall of the blood vessel proximate the thrombus site, the first set of helicoidal filaments forming a second angle with the second set of helicoidal filaments in the delivery configuration, the second angle being greater than the first angle; expanding the second section of the thrombus extraction device into a conically shaped deployment configuration with a second outward radial force less than the first outward radial force sufficient to stop proximal blood flow, a proximal end of the second section having a smaller diameter in the deployment configuration than a distal end of the second section; and aspirating a thrombus into the thrombus extraction device.

In some such embodiments, the method also includes the optional step of supporting the proximal end of the first section with a distal end of the second section. In some or all of these embodiments, the step of expanding the first section includes the step of applying spring force to a distal of the first section with closed ends of the helicoidal filaments.

The first outward radial force can be uniformly distributed along the first section in the deployment configuration. Alternatively, the first and second end portions of the first section have outward radial forces in the deployment configuration greater than an outward radial force of an intermediate portion of the first section in the deployment configuration.

The thrombus extraction device may optionally include a coating over the first and second sections, in which case the reducing step of some or all of these methods may include the step of permitting blood to flow through holes in the coating.

Some embodiments may include the optional step of, after the aspirating step, moving the thrombus extraction device from the deployment configuration to a capture configuration (i.e. when the thrombus is inside) in which the first and second sets of helicoidal filaments form a third angle less than the second angle.

The thrombus extraction device may optionally include a catheter attached to a proximal end of the second section, in which case the aspirating step of some or all of these methods may include the step of applying a vacuum through the catheter to interior spaces of the first and second sections.

Advantages of the device derived from its structure and the parameters described herein, can be summarized as follows:

Adequate radial force to stop the blood flow and for the device to expand;

"Chinese finger trap" effect: this phenomenon occurs when an axial force is applied by pulling the device backwards or when the device contacts the vessel so the device is retained or braked. If there is an object inside (e.g. the thrombus), the device tends to lengthen and therefore decreases its diameter, causing a compression which helps to retain the thrombus inside the device. This effect is achieved by the device of the invention also thanks to the fact that there are no welding points between filaments, so the device can easily lengthen and trap the thrombus;

Pushability: when the mesh is compressed inside the carrier, the filaments are aligned longitudinally so that the spring effect is avoided and the movement inside is facilitated. As indicated, the closed loops at the distal end also contribute to a correct pushability related to an adequate navigability of the device within the blood vessels.

Conformability inside the blood vessels, achieved mainly by the angle between filaments of the mesh that favor the adaptation of the mesh to the curves of the vessels and avoiding kinking of the device.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PARTICULAR EMBODIMENTS

Figure 1:
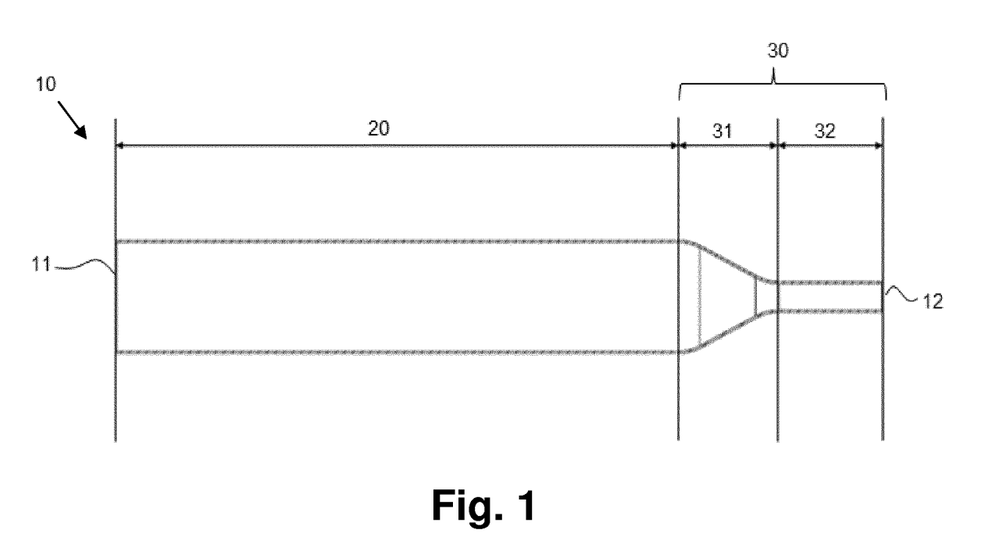
FIG. 1 schematically illustrates the different sections included in the proposed device for extraction of thrombus from a blood vessel, according to an embodiment of the present invention.
Figure 2:
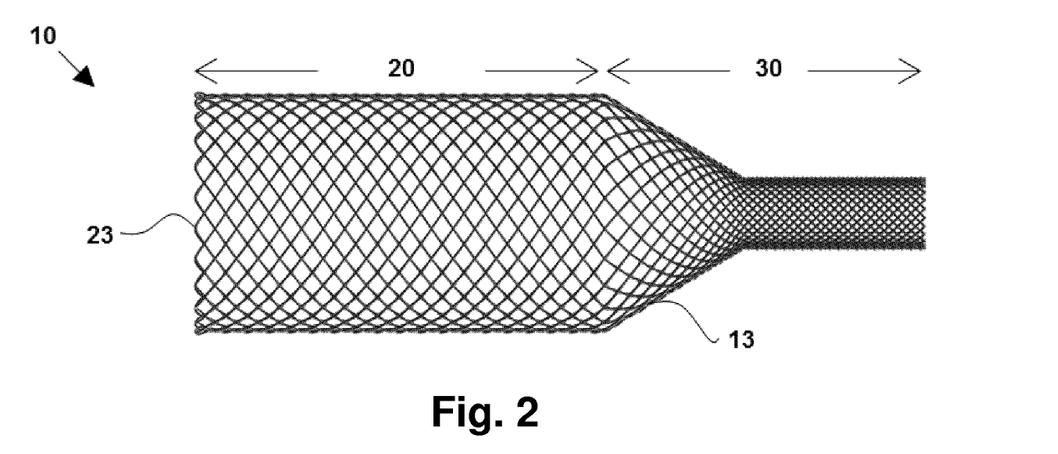
FIG. 2 illustrates the mesh included in the different tubular sections of the proposed device having a lower mesh density in the first section than in the second section.

FIGS. 1 and 2 show particular embodiments of the proposed device for extraction of thrombus from a blood vessel. The proposed device includes a segment 10 which is self-expandable and defines a distal end 11 and a proximal end 12 and can adapt its shape to a surrounding blood vessel from a retracted position in a compressed state, for example inside a carrier such a delivery catheter (not shown), to an extended/expanded position, once coming out of the carrier, to be appositioned against the inner wall of a blood vessel to receive and retain a thrombus.

As shown in FIG. 2, the segment 10 comprises a mesh 13 having two sets of helicoidal filaments turning respectively in opposite directions and being intertwined. The mesh 13 in an embodiment can follow a diamond-type structure or a regular structure. The density of the mesh 13 defines the elasticity of the segment 10. As detailed in Table 1 the mesh angle (or braiding angle ($\beta$)) with regard to a longitudinal direction can be variable.

The helicoidal filaments can be made of a metal (including metal alloys), polymers, a composite including Nitinol or Nitinol/Platinum, or also DFT$^R$ (Drawn Filled Tube), among other materials having suitable mechanical properties.

As can be seen in the FIGS. 1 and 2, the mesh 13 defines two distinct tubular sections, a first section 20 and a second section 30. Particularly, the second section 30 comprises two sub sections, a first sub section 31 and a second sub section 32.

As can be seen in FIG. 2, in this particular embodiment, the end portion of the first section 20 at the distal end 11 comprises closed loops 23 facilitating the expansion of the segment 10 once it comes out of the cited carrier. Moreover, these closed loops 23 act as a spring or fixing point by limiting the movement between the helicoidal filaments and thus increasing the outward radial force. The closed loops 23 also provide a smooth distal end to reduce possible vessel damage and improve navigability of the device within the blood vessel. The rest of the first section 20 creates the space which will accommodate the thrombus once it has been aspirated. The first section 20 is adaptable to the vessel geometry and, because of its configuration (e.g., diameter and braiding angle), provides outward radial forces higher than in the second section 30 so that the segment 10 is better appositioned against the inner wall of the vessel. The radial forces in the end portions of the first section 20 are particularly higher than in an intermediate portion thereof, e.g., because of the spring action of closed loops 23. Alternatively, the radial forces in the first section 20 could be uniformly distributed along all its generatrix.

The first sub-section 31 (or portion of the second section 30 adjacent to the first section 20) is cone-shaped or funnel-shaped. Because of its shape, this sub-section 31 has features enabling it to withstand the blood pressure without collapsing. In the illustrated embodiment, the braiding angle (a) changes at the proximal and distal ends of sub-section 31 provide radial strength to maintain the conical shape. The braiding angle (a) change at the distal end of sub-section 31 also works with the closed loops 23 to maintain first section 20 in an open position and create the space for the thrombus. The covering over sub-section 31 stops the blood flow during the capture and removal of the thrombus and protects the captured thrombus during the withdrawal of the segment 10 to the carrier. This sub-section 31 is also the transition from the larger diameter of section 20 to the smaller diameter sub-section 32 for connection to an aspiration catheter or a hypotube (not shown).

The second sub-section 32 (or portion of the second section 30 adjacent to proximal end 12) has a tubular uniform diameter and provides the connection to the aspiration catheter or to the hypotube. In some embodiments, the aspiration catheter is a PTFE-lined braided catheter covered by an outer jacket. The aspiration catheter's braid and liner extend distally from the outer jacket. A layer of polymer material may be placed around the protruding braid and liner, and a mandrel may be placed within the braid and liner. Thereafter, the second sub-section 32 of segment 10 may be placed over this polymer section, and another layer of polymer may be placed over the mesh of subsection 32. This outer layer of polymer material is then melted so that polymer flows through the cells of the mesh 13, the mandrel is removed, and a smooth surface is left over the entire aspiration catheter. This attachment approach adds structure and stiffness to the attachment section of the aspiration catheter, so it should be as short as possible without compromising the integrity of the attachment of segment 10 to the catheter.

Other techniques of connecting segment 10 to an aspiration catheter may be used, as understood by skilled artisans. For example, in other embodiments, if the aspiration catheter is a metal hypotube, the mesh 13 of the sub-section 32 is welded to a Nitinol ring. This ring is welded directly to the hypotube. Alternatively, a Stainless-steel ring can be glued to the mesh 13 of the sub-section 32. Then, the Stainless-steel ring is welded to the hypotube. Another option is to directly mesh the segment 10 over a perforated ring so that the filaments pass through the holes.

When the segment 10 is compressed inside the carrier, segment 10 elongates to move the helicoidal filaments toward a longitudinal alignment so as to reduce the spring effect and to facilitate the movement of segment 10 within the carrier by reducing friction effects and by increasing pushability. The pushability of the segment inside the carrier is related to the navigability of the segment 10 within the arteries.

The mesh angle (13) allows the mesh 13 to be adapted to a curve of the blood vessel, avoiding the kinking and creating a free space inside the mesh for unobstructed suction.

Figures 3A, 3B, 3C:
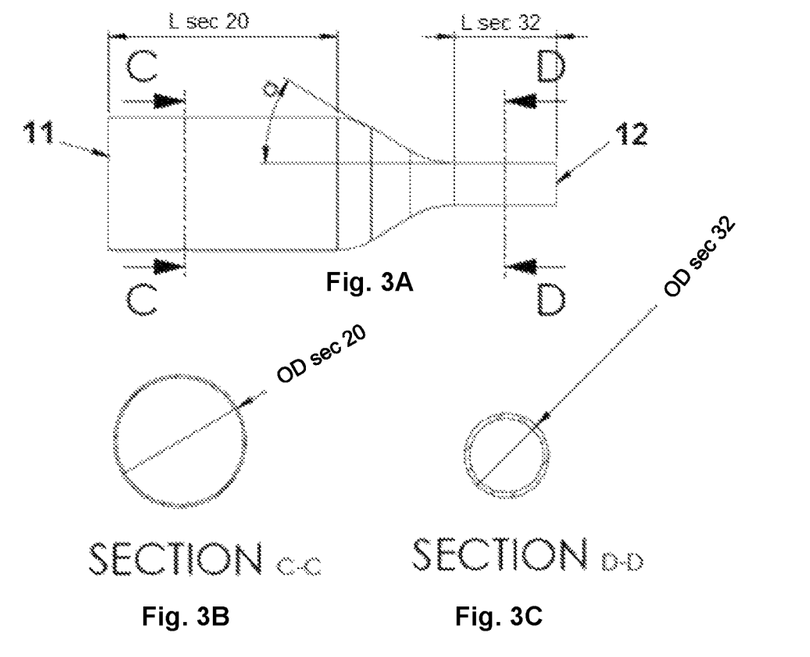
FIGS. 3A-C schematically illustrate some of the main specifications of the proposed device.

With reference now to FIG. 3 therein are illustrated some of the main specifications of the device according to an embodiment. Table 1 indicates the main specifications of the device. Table 2 indicates the measuring method used for calculating such parameters.

TABLE 1

Main specifications of the device

| | | Example | Range | Big Ref. | Small Ref. |
|---|---|---|---|---|---|
| Shape parameters | OD sec 20 [mm] | 6 | 3.5--6 | 5.2 | Approx. 4.1 |
| | OD sec 32 [mm] | catheter OD | 1--2 | 1.65 | 1.65 |
| | L sec 20 [mm] | 15 | 4--40 | 9 | 4-8 |
| | α sec 31 [°] | 45 | 15--45 | 31 | 20 |
| | L sec 32 [mm] | 2 | 1--10 | 3.5 | 3 |
| Braiding parameters | Wire OD [μm] | 50 | 40--60 | 51 | 51-58 |
| | Wire number | 48 | 24--48 | 48 | 24-36 |
| | β sec 20 [°] | 60 | 50--65 | 55 | 65 |
| | β sec 32 [°] | 20 | 15--50 | 45 | 45 |

Table 1 shows the parameters for particular embodiments. In an embodiment, the parameters of the device are such indicated in Table 1 for a big blood vessel ("Big Ref.") of e.g. 4.5 mm diameter, such as the final part of the carotid or the carotid siphon. In another embodiment, the parameters of the device are such indicated in Table 1 for a small blood vessel ("Small Ref.") of e.g. 2.5 mm diameter, such as the Internal Carotid Artery (ICA) or the Middle Cerebral Artery (MCA).

TABLE 2

Measuring methods used for calculating the different parameters.

| Parameter | Measuring method |
|---|---|
| OD sec 20 [mm] | The mandrel on which the proposed device is meshed is measured. It is a solid piece with the same shape as the stent. The final diameter is determined by measuring the diameter of the solid piece and adding 4 times the diameter of the helicoidal filaments/wires. |
| OD sec 32 [mm] | Same as before |
| L sec 20 [mm] | Same as before |
| α sec 31 [°] | Same as before |
| L sec 32 [mm] | Once the proposed device has been meshed, it is placed on a tool that determines where the excess length should be cut. |
| Wire OD [μm] | It is measured with a precision measuring instrument. |
| Wire number | Alternative 1: Counting the number of distal loops and multiplying by 2<br>Alternative 2: Counting the number of reels used for meshing |
| β sec 20 [°] | Alternative 1: Measuring the number of wire crossings in a given length measured in the axial direction.<br>Alternative 2: If the mandrel is manufactured with grooves so that during the meshing the wires are inserted inside and the manufacturing is improved, it is simply measured that the mandrel is manufactured with the appropriate parameters. |
| β sec 32 [°] | Same as before |

As mentioned, the device may be in two configurations: in a retracted form (or compressed state) inside the carrier while approaching the thrombus site, and in an extended and expanded (deployed) form when there is no interaction with the carrier or the blood vessel. The parameters specified herein relate to the device in its natural (relaxed) form; i.e. extended and expanded (deployed) position.

The segment 10 may include radiopaque markers made of platinum, tungsten, barium derivatives, gold, iridium, among others, at its distal end 11 and/or other strategic points within the mesh 13 which allow a physician to know the precise location of the device while using fluoroscopy. The radiopaque material can be deposited on the helicoidal filaments once manufactured (if the device has a coating, the material may also be dispersed on the surface of the coating). Alternative possibilities to confer radiopacity to the segment 10 are using helicoidal filaments of different material and opacity grade (e.g. Nitinol and Platinum). In a particular embodiment, Nitinol wires with a Platinum core are used. Likewise, the delivery catheter may also include radiopaque markers.

Moreover, the segment 10 may have a coating, for example covering the first section 20 only or covering the whole segment 10. In the embodiments of FIGS. 1 and 2, although not seen, the coating goes from the closed loops 23 to sub-section 32. In one embodiment, the coating is applied about attachment of segment 10 to an aspiration catheter by dipping segment 10 into a liquid polymer, the allowing the polymer to solidify. Optionally, a mandrel may be disposed inside the mesh 13 of segment 10 when it is dipped into the polymeric coating material. Alternatively, the coating material may be sprayed onto the mesh. In other alternative embodiments, the coating may be applied before attaching segment 10 to an aspiration catheter. In such embodiments, the coating does not reach the proximal end 12 of sub-section 32, but there is an uncoated space between the helicoidal filaments, leaving them free to allow assembly with the aspiration catheter.

The coating prevents damage to the arteries, avoiding direct contact with the helicoidal filaments. Moreover, the coating provides a watertight compartment so that the thrombus can be sucked in and protected during removal. In an embodiment, to apply the coating, the mesh 13 is attached to the carrier or delivery catheter and then the coating is applied.

An interior or exterior glaze can be also applied to the coating to improve its properties. By applying a hydrophilic or hydrophobic coating to the exterior surface of the segment 10, the exterior surface can be more easily displaced into the carrier and through the blood vessel by reducing the coefficient of friction. In the same way, by applying a treatment in the interior surface of the segment 10 an adhesion effect that retains the thrombus once it is inside can be achieved.

The coating is made of an elastic material. In one particular embodiment, the device coating is silicone. Alternatively, polyurethanes or other types of plastic materials can be used. A blend of polyurethane and silicone may also be employed.

To achieve the double behavior of the coating (lubricious on the exterior surface of segment 10 and tacky or rough inside), the coating can be treated by the addition of a material as explained, or can have constitutively such features by the structure of the mesh itself.

The coating can include holes to avoid collapse of the segment 10. Such holes may be formed after the coating has been applied by perforating the coating.

Figure 4:
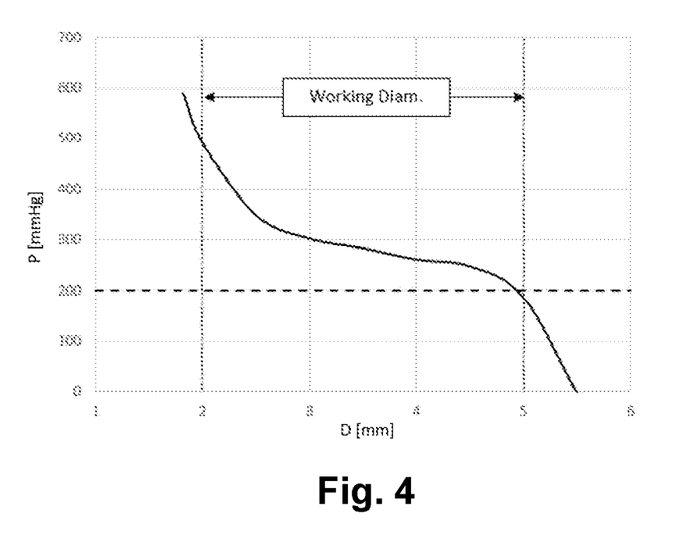
FIG. 4 is a graph showing Ideal pressure vs. diameter curve of the proposed device.

The dimensions of segment 10 depend on the dimensions of the blood vessel in which it will be used to capture a thrombus. The dimensions of the sub-sections of segment 10 and the braid angles of the mesh help segment 10 provide a reduced radially outward force when compressed into the delivery catheter and sufficient outward force when expanded to avoid collapse from the blood pressure. FIG. 4 illustrates a possible work curve of one embodiment of the segment 10. Y-axis defines the device pressure (mmHg) whereas X-axis defines the diameter of the arteries (mm). The horizontal dotted line marks the blood pressure limit. In some embodiments, the diameter range of the arteries in which the device of this invention may be used is 2 to 5 mm. The segment 10 is designed so that it can expand without being blocked by the artery working in a standard range of 2 to 5 mm and so that it can cope with a blood pressure greater than 200 mmHg. As shown by FIG. 4, this particular embodiment is not designed to be compressed to a diameter less than 2 mm. Compression of the segment 10 within the delivery catheter may result in radially outward forces high enough to inhibit advancement of the device within the carrier.

Figure 5:
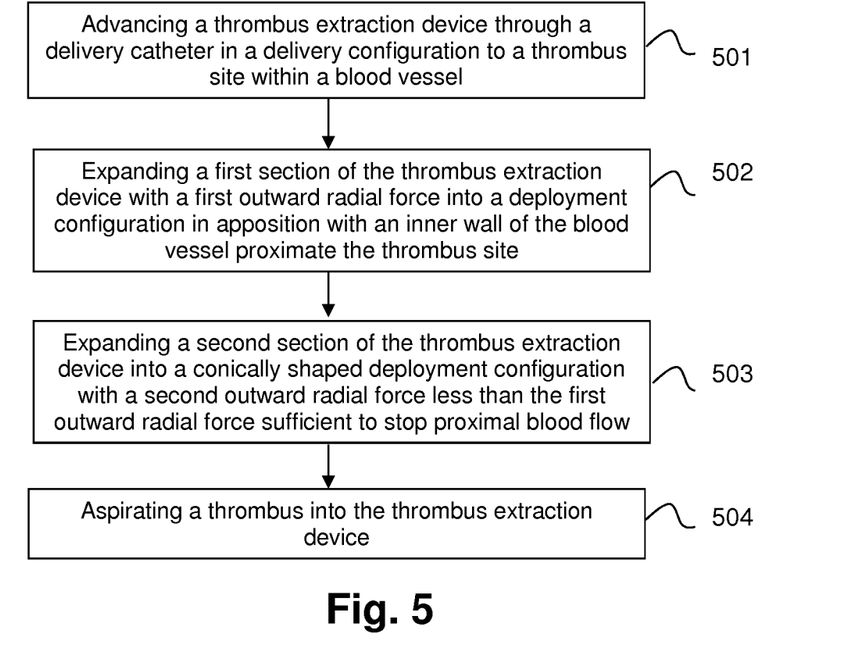
FIG. 5 is a flowchart illustrating a method for extracting a thrombus from a thrombus site in a blood vessel of a patient, according to an embodiment of the present invention.

With reference now to FIG. 5, therein it is illustrated an embodiment of a method for extracting a thrombus from a thrombus site in a blood vessel of a patient. According to this particular embodiment, the method at step 501 comprises advancing a thrombus extraction device through a delivery catheter in a delivery configuration to a thrombus site within a blood vessel. The thrombus extraction device comprising a mesh 13 of at least first and second sets of oppositely wound and intertwined helicoidal filaments having a first section 20 at a distal end 11 and a second section 30 extending proximally from a proximal end 12 of the first section 20, the first set of helicoidal filaments forming a distally facing first angle with the second set of helicoidal filaments in the delivery configuration. At step 502, the method comprises expanding the first section 20 of the thrombus extraction device with a first outward radial force into a deployment configuration in apposition with an inner wall of the blood vessel proximate the thrombus site, the first set of helicoidal filaments forming a second angle with the second set of helicoidal filaments in the delivery configuration, the second angle being greater than the first angle. Then, at step 503, the method comprises expanding the second section 30 of the thrombus extraction device into a conically shaped deployment configuration with a second outward radial force less than the first outward radial force sufficient to stop proximal blood flow, a proximal end of the second section 30 having a smaller diameter in the deployment configuration than a distal end of the second section 30. Finally, at step 504, the method comprises aspirating a thrombus into the thrombus extraction device.

Embodiments of the present invention also provide a thrombectomy apparatus 600 for extraction of thrombus from a blood vessel including the proposed segment 10 of any of the described embodiments.

Some embodiments of the invention may be automated for use in traditional (hospital) and non-traditional (nursing home, assisted care facility) environments which may allow for greater deployment and usage of the present invention and hasten the removal of thrombus, thus significantly improving patient outcomes, as flow may be restored (e.g., to critical areas of the brain) within much shorter times. One such automated device is illustrated in WO2016/113047.

In use, segment 10 and the aspiration catheter or hypotube to which it is attached are advanced through a delivery catheter to a thrombus site within a blood vessel of the patient. During advancement in the delivery catheter, the segment 10 is in a delivery configuration in which the first and second sets of helicoidal filaments form a first distally facing angle with respect to each other. When segment 10 emerges from the delivery catheter, it begins to self-expand to a deployment configuration. In embodiments in which the mesh forms closed loops at the distal end of segment 10, the spring action of the closed loops of the helicoidal filaments helps the first section 20 expand into apposition with the blood vessel proximate to the thrombus site. In the deployment configuration, the first and second sets of helicoidal filaments form a second distally facing angle less than the first angle (i.e., the filaments are less longitudinally aligned in the deployment configuration than they were in the delivery configuration). Sub-section 31 also self-expands to a conical or funnel shape. The distal end of sub-section 31 helps support the proximal end of section 20 in its deployment configuration.

The coating on the outside of sub-section 31 and section 20 reduce blood flow to the thrombus site. The optional holes through the coating permit a small amount of blood to pass through the device to avoid collapse of sub-section 31 caused by the blood pressure and also by the difference of pressure between the blood pressure (externally) and the vacuum applied (internally). Once blood flow has been reduced, suction may be applied through the catheter or hypotube to the interior spaces of sub-section 31 and section 20 to aspirate the thrombus into section 20. Device 10 capturing the thrombus may then be removed from the patient. In the capture configuration (i.e. when the thrombus is inside), the first and second sets of filaments form a third distally-facing angle less than the first distally-faced angle (i.e., the filaments become more longitudinally aligned) as the device assumes a longer and smaller diameter shape.

Figure 6:
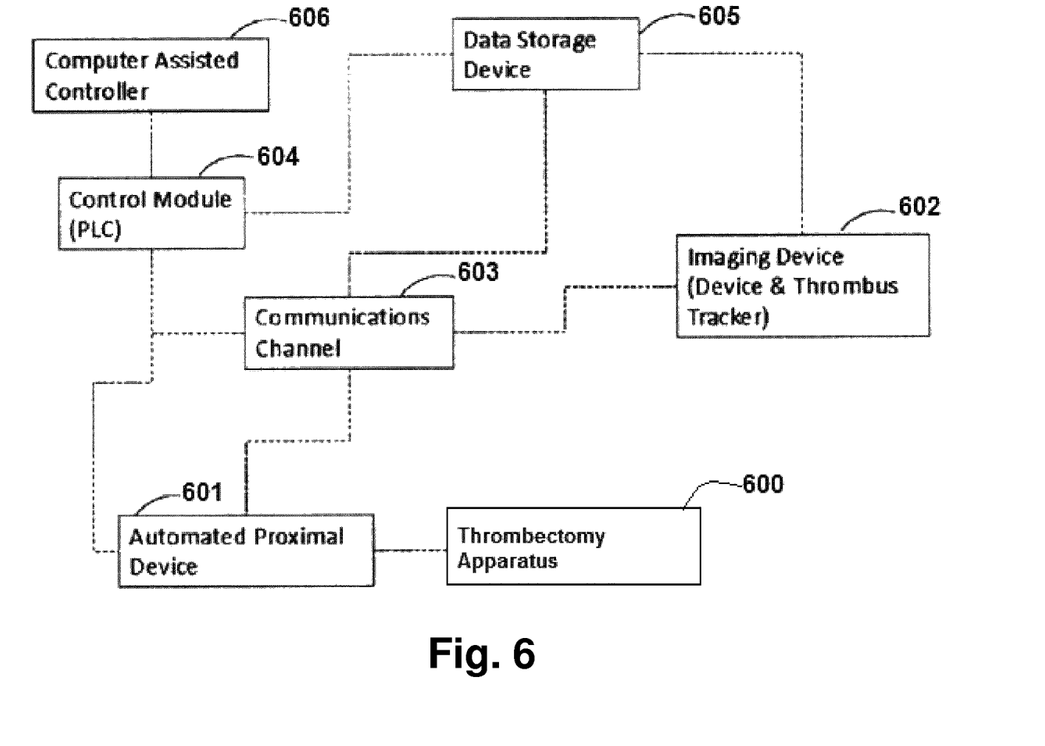
FIG. 6 is a diagram illustrating an automated thrombectomy apparatus according to the present invention.
Figure 7:
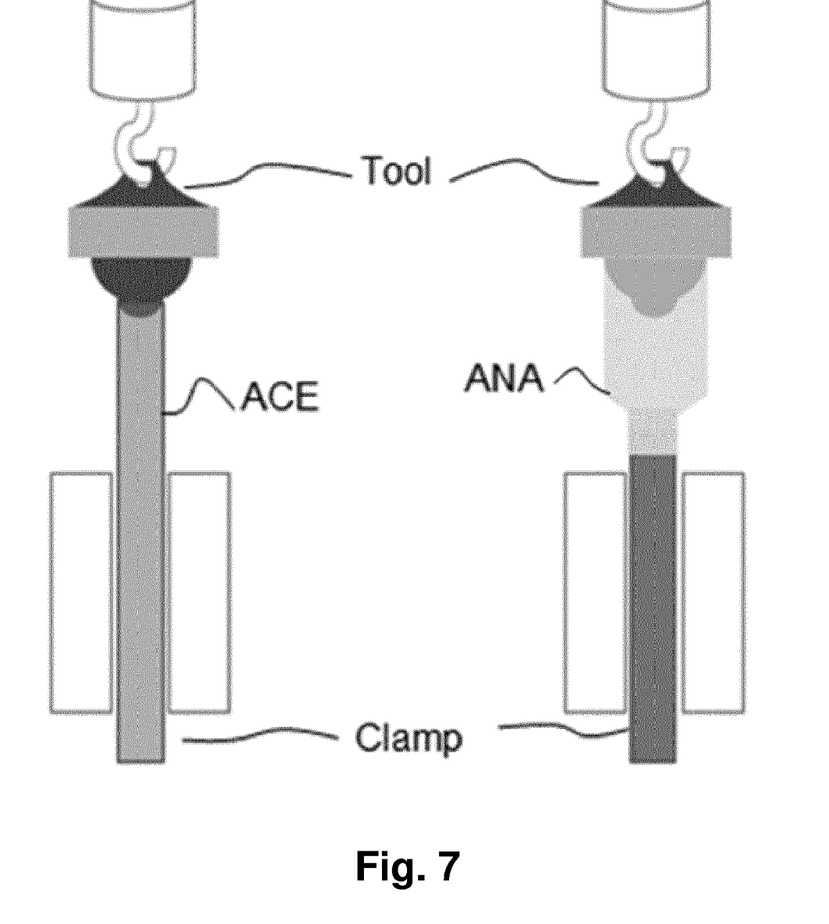
FIG. 7 schematically illustrates the experimental setup model used in example 2 in order to evaluate the force in the tip of the catheter.

FIG. 6 depicts an example of the thrombectomy apparatus 600 of the present invention which allows for the automated maneuvering of the thrombectomy apparatus 600 through a vascular system.

According to this particular example, an automated proximal device 601 provides a guidance system to deploy the thrombectomy apparatus 600. Moreover, an imaging device 602 can detect the radiopaque markers included in the segment 10, and also in the delivery catheter, and a communications channel 603 can be used to provide means to transport the image to a control module 604. The control module 604 is programmed or configured to allow for guidance of the deployment of the thrombectomy apparatus 600 and storage of data on a data storage device 605. The control module 604 may be a programmable logic controller, a computer, or the like. In this particular embodiment the control module 604 is guided by a computer assisted controller 606. The communications channel 603 can be Ethernet, WiFi, Bluetooth, or the like. The control module 604 is programmed to guide a physician or technician operating the thrombectomy apparatus 600 which allows for the thrombectomy apparatus 600 to be used in non-hospital settings such as nursing homes or assisted care living facilities.

By allowing the thrombectomy apparatus 600 to be used "in the field" the time required to perform the thrombectomy is greatly reduced significantly improving patient outcomes. The control may also be via a controller such as those in use in other current medical devices. In another embodiment, the system may be controlled manually.

Following, two particular experimental examples of the thrombectomy apparatus (also referred as ANCD device) comprising the Advanced Neurovascular Aspiration catheter (also referred as ANA catheter) are detailed.

Example 1: In Vivo Assay: Chronic Evaluation of Performance and Safety of the ANCD Advanced Flow Restriction System in a Swine Model Introduction Endovascular treatment (EVT) is recognized as the most effective treatment for large vessel occlusion (LVO) strokes. Highest degree of recanalization in the shortest time with the minimum number of attempts have been demonstrated to correlate with improved clinical outcomes. Although highly effective, failure to reach complete recanalization has been reported in about 20% of treated patients. In order to improve patient outcomes, different devices and combinations are under development to increase the first pass complete recanalization rate. The development of such devices includes preclinical testing in phantom models simulating the cerebrovascular human anatomy, and animal models in which device related vessel injury can be assessed. Each simulation model has its own characteristics and therefore it is recommended that any new device or combination will prove its efficacy and safety in different conditions before final evaluation in a first in human study.

The Advanced Thrombectomy System (ANCD) is a novel stroke thrombectomy apparatus that includes the proposed device for extraction of thrombus from a blood vessel, a self-expanding radiopaque braid covered by a continuous polymeric coating, designed to reduce clot fragmentation and facilitate retrieval by inducing local flow restriction and allowing distal aspiration.

The aim of this study was to evaluate the pre-clinical efficacy and safety of the ANCD, in a swine model 3 and 30 days following 3 passes, and specifically confirm that the use of the novel self-expanding funnel is unrelated to higher vascular injury in comparison with a commonly used device, the FlowGate™ Balloon Guide Catheter.

The acute performance and safety on day 0 (performance-usability endpoints, devices integrity and angiography) and the safety data (angiography, histology and health monitoring) after 3 and 30 days, respectively, were studied.

Methods:

Description of the ANCD Device

The ANCD is a thrombectomy apparatus that is comprised of two coaxial catheters: a funnel catheter and a delivery catheter.

The funnel catheter is comprised of highly flexible polymers onto a braided metallic structure. It is intended to restrict locally the blood flow during the intervention. It is composed of a self-expanding funnel that, when unsheathed, can expand to the diameter of the blood vessel, adapting to its shape, thereby restricting the blood flow. The funnel catheter can provide an effective aspiration that serves as a complementary mechanism when combined with retrieval devices. The funnel is designed to have enough flexibility to adapt to the neurovascular tortuosity. The funnel is comprised of a radiopaque braid and a polymeric film.

The delivery catheter is the outermost catheter of the device, which navigates until reaching the target vessel. It has a hydrophilic coating to reduce friction during use and a radiopaque marker on the distal end for angiographic visualization. The materials of the catheter allow enhanced flexibility in the tip and sufficient stiffness and pushability of the proximal portion.

FlowGate™ Balloon Guide Catheter is a common commercial device which offers proximal flow control and a stable platform to facilitate the insertion and guidance of an intravascular catheter. It provides a balance of trackability and support with a large lumen and is indicated for use as a conduit for retrieval devices.

Animal Model

All animals were held in quarantine and housed at CBSET (Lexington, MA, USA), where the study was conducted, a facility accredited by the American Association for Accreditation of Laboratory Animal Care, under conditions that met or exceeded requirements as set forth in the USDA guidelines. Standard veterinary practices were performed during quarantine, including physical examinations and clinical pathology to determine health status before assignment to the study. A nutritionally balanced diet appropriate for the species was offered daily to all animals with water ad libitum.

Eleven pigs were used in this study (female or castrated male Yorkshire pigs, weight 39-50 Kg). The swine model was chosen as the experimental species for this study because the size and anatomy of the vascular system is clinically relevant for the purpose of testing catheter-based medical devices for the treatment of vascular disease. Also, swine is an established animal model for vascular studies and generally accepted as a scientific standard.

Animals were anesthetized, intubated, and IV catheterized for the administration of supportive IV fluids and medications. The surgical procedures were performed under aseptic conditions. Physiological parameters were monitored through all the procedures. The femoral artery was accessed via cutdown approach. A 9 F introducer sheath was advanced into the artery and heparin (150 U/kg, IV) was administered to prolong Activated Clotting Time (ACT) to approximately 200-350 seconds. ACT levels were monitored every 45 minutes during all the procedures, and additional heparin was administered as needed to maintain the target ACT. Under fluoroscopic guidance, an 8F Mach 1™ guide catheter (CGC: Boston Scientific, Marlborough, MA) was advanced through the sheath over a guide wire into the descending aorta and to the target arteries. Angiographic images of the vessels were obtained with contrast media to identify a suitable location for the treatment site. Angiograms were performed throughout the procedure: baseline, after each pass, and prior to necropsy. The parameters assessed by angiography (qualitative and quantitative) were: vessel anatomy, target site, device monitoring, vessel status-injury, vasospasm, and blood flow (mTICI scale).

The two devices were used per Instructions for Use (IFU) for the interventions of the target vessels:

1—BGC: Balloon Guide Catheter (BGC: 8Fr FlowGate2™ Balloon Guide Catheter (95 cm); from Stryker Neurovascular, Fremont, CA), and
2—ANCD: ANCD (Anaconda Biomed) through the guide catheter CGC.

Renal, cervical and lingual arteries were targeted. These arteries cover the diameter range between 2.2 and 5 mm for ANCD, and 2.7 to 5 mm for the BGC, which represents the size of the target vessels in the cerebrovasculature (internal carotid artery (ICA), middle cerebral artery (MCA)).

ANCD and BGC devices were distributed among target vessels to ensure assessment was made in all vascular beds at each time point. Randomization of animals was not required for this study as each animal had both ANCD and BGC devices evaluations.

In order to study the devices in a clinical simulation as a worst case scenario, three passes in every study group were assessed in all cases. The potential vascular injury caused by the devices (perforation, dissection, thrombosis) and vasospasm was also assessed during the procedure by angiography.

Thrombectomy Procedures

Intravascular devices were maneuvered under fluoroscopic guidance and angiographic images of the vessels were obtained to identify the proper location of the device. In intervention 1, the BGC was inflated to arrest flow, as per IFU and usual practice, aspiration was applied through the BGC. In intervention 2, the ANCD catheter system was advanced close to the target vessel site and the funnel deployed creating local flow arrest. In all interventions, aspiration during the thrombectomy procedure was performed with a 60 cc syringe (Vaclock; Merit Medical) connected to a three-way stopcock through either the BGC (intervention 1), or the ANCD funnel catheter (intervention 2).

The resulting study design is summarized in the following Table 3:

TABLE 3

Study design: Testing devices (ANCD and FlowGate BGC), number and location of vessels, number of animals involved and time point assessments.

| Test/Control Device | Number of Vessels/ Treatment Scheme | | Number of Animals | Time Point |
|---|---|---|---|---|
| ANCD | Renal arteries n = 5 Cervical or lingual arteries n = 3 | n = 8 | 5 | Day 3 |
| FlowGate BGC | Renal arteries n = 5 | n = 5 | | |
| ANCD | Renal arteries n = 6 Cervical or lingual arteries n = 4 | n = 10 | 6 | Day 30 ± 2 |
| FlowGate BGC | Renal arteries n = 6 | n = 6 | | |

Acute performance evaluations on the day of procedure included user interface and ability to maneuver the device. The potential vascular injury caused by the devices was also assessed during the procedure by angiography.

Histopathology

Animals were euthanatized after 3 and 30 days and underwent a comprehensive necropsy. Treated vessels were dissected and relevant tissues/organs were collected, fixed in 10% NBF (Neutral Buffered Formalin) and paraffin embedded and stained with H&E (hematoxylin and eosin) and Verhoeff's for histomorphologic assessment. Each treated vessel was trimmed to yield at least six cross-sections (2 proximal, 2 mid and 2 distal) within the putative area of treatment. For lingual treatments, the treated vessel sections were taken from the breadloafed tongue sections and may include surrounding parenchyma. Additionally, untreated distal sections of the vessel were obtained within approximately 5 mm of the distal end of the putative treated area.

Light microscopy was used to determine histomorphological scoring of parameters that reflected the degree and extent of the host response/repair process to the treatment in target vessels. Histomorphometric markers included: vascular injury, vascular mural compression lesion, inflammation, endothelization, luminal fibrin/thrombus deposition, neointima formation, and adventitial fibrosis. Histologic sections of vessels were also examined for other microscopic changes including hemorrhage, necrosis, and type and relative amounts of inflammatory cell infiltrates. Sections of representative downstream tissues were evaluated for any adverse effects associated with treatment, including thrombosis, necrosis, inflammation and presence of embolic material. Scoring values were calculated for every section and level and reported as an overall mean of each vessel, ranking from 0 (no injury) to 3 (highest possible degree of injury) in all markers except for endothelization than ranked from 0 (absence of endothelial covering) to 4 (complete endothelial covering). The pathologist was blinded to the treatment matrix at the time of the pathologist read.

Results:

The ANCD navigability and pushability through vessel curvatures was better compared with the FlowGate BGC.

The funnel of the ANCD device performed adequately in most cases, with complete deployment, accuracy and adaptability to vessel curvatures, and significant reduction of the antegrade blood flow.

The ANCD device avoided kinking during the navigability and deployment on the target vessel.

The ANCD device was able to complete the 3 passes with correct performance and maintained its general integrity. Radiopacity, withdrawal of the catheter and hemostasis were adequate.

During interventions, the devices could potentially generate clots in situ due to the interaction with blood. After the interventions of the present study, no thrombus was observed on the catheters or funnels surfaces after removal from the body, supporting the adequate thromboresistance of both devices.

No vessel perforation, dissections, or occlusions were observed. Vasospasm was a common observation to varying degrees for both test and control devices. This is a common observation in the swine model as pigs are prone to vasospasm.

Histomorphologic markers of vascular injury after 3 and 30 days, respectively, were absent to minimal across all groups, and generally improved over time. Downstream tissues showed sparse and minimal evidence of embolic material and was not correlated with necrosis or other evidence of circulatory compromise in the target organs. Findings of embolic foreign material was minimal and was similar across treatment groups, indicating a shared origin, and was most consistent with lubricious coating used on various ancillary products. Other findings, like inflammation, thrombosis and necrosis were absent to minimal in all groups and time points.

All animals survived to their scheduled time point. Clinical observation of the animals, body weight evolution, blood analysis and necropsy did not reveal signs of clinical abnormalities related to the ANCD or FlowGate devices for any study animal.

Conclusions

The ANCD device showed an excellent performance, with a complete deployment and accuracy, in intravascular interventions, similar to the control device FlowGate BGC.

The ANCD device performed better than the control device, in terms of navigability, pushability and adaptability in vessel curvatures. Also, showed a significant reduction of the antegrade blood flow.

The ANCD device groups showed minimal vessel injury and similar to FlowGate BGC groups, and it improved over time.

Downstream tissues to treated vessels showed minimal or absence of lesions, similar in the ANCD device and FlowGate BGC groups.

The ANCD device showed a favorable safety profile based on the absence of systemic and local adverse effects in treated animals.

Example 2: Suction Force Aspiration Test of the Advanced Neurovascular Aspiration (ANA) Catheter Introduction The endovascular treatment of ischemic stroke involves a wide range of devices and techniques. The aspiration thrombectomy technique is intended to restore blood flow in patients experiencing acute ischemic stroke due to vessel occlusion by applying a suction force to remove the clot. This research is aiming to analyse the suction-forces over the clot of two different catheter designs using experimental analysis. To study the suction tip-force, the clot was considered as rigid. For that purpose, the force generated by the tip of the ACE68 Reperfusion Catheter (Penumbra Inc, hereinafter referred as ACE), and the ANA Advanced Neurovascular Aspiration catheter (Anaconda Biomed, hereinafter referred as ANA) were evaluated using a tensile tester machine and special designed tools that completely cover the tip of the device in order to simulate a complete occlusion of the clot.

ANA is a funnel catheter comprised of highly flexible polymers onto a braided metallic structure. It is intended to restrict locally the blood flow during the intervention. It is composed of a self-expanding funnel that, when unsheathed, can expand to the diameter of the blood vessel, adapting to its shape, thereby restricting the blood flow. The funnel catheter can provide an effective aspiration and it can be used as a complementary mechanism when combined with retrieval devices. The funnel is designed to have enough flexibility to adapt to the neurovascular tortuosity. The funnel is comprised of a radiopaque braid and a polymeric film.

ACE is a reperfusion catheter comprised of a coil-winding geometry along 16 transitions. It is intended to create an optimal tracking profile to facilitate clot extraction from proximal large vessels with the vacuum power of the Penumbra Pump MAX™ associated to the catheter.

Methods:

The test was performed with the purpose of analysing thrombus suction-forces and stresses induced by different aspiration devices for the treatment of ischemic stroke. In order to evaluate the force in the tip of the catheter the experimental model shown in FIG. 6 was defined.

The INSTRON-EQ152 tensile tester with 10N load cell was used. A specially designed tool was connected to the load cell, tool that was capable of occluding the inner tip diameter of the two catheters (units) selected for this study (ANA and ACE). Once the tip covered the tool, a negative pressure of 500 mmHg was applied using a VacMaxi Pump (APEX) intended for suction catheters. Then a constant speed of 50 mm/min was applied and the force necessary for the separation of the tool was evaluated.

Regarding the design selected for the tooling, it was intended to reduce the friction forces produced by the collapse of the tip during the aspiration. This phenomenon could have a higher impact in the ANA catheter due to the flexible braided structured design of the tip, that could lead to a closer contact with the wall of the tool. The authors considered that this fact could have a potential benefit in the clinical practice creating a trap for the clot when it is inside the catheter tip.

Results and Conclusions

The results obtained in the test are presented in the following Table.

TABLE 4

| | Experimental results | | |
| --- | --- | --- | --- |
| Device | Force (N) | Standard deviation | Variance coefficient (%) |
| ACE | 0.11 N | 0.04 | 39% |
| ANA | 0.42 N | 0.06 | 14% |

Based on the results it can be stated that the force experimented in the tip when a rigid surface is completely occluding the inner diameter, is more than three times higher in the ANA than in the ACE catheter. This study represents an approach clinically relevant of what happens in a scenario in which a hard thrombus (rigid material) is completely occluding the tip of the catheter. The features of ANA funnel, mainly its bigger and more flexible tip, create an efficient suction trap avoiding the separation of the clot from the catheter at higher forces than the ACE device.

Although illustrated and described above with reference to certain specific embodiments, the present invention is however not intended to be limited to the details shown. Rather, various modifications may be made in the details within the scope and range of equivalents of the claims.

The scope of the present invention is defined in the following set of claims.

What is claimed is:

1. A device for extraction of thrombus from a blood vessel, said device comprising a segment defining a distal end and a proximal end and being configured to change its shape from a retracted position in a compressed state to an extended and expanded position, to be appositioned against an inner wall of the blood vessel, to receive and retain the thrombus, wherein the segment is formed by a mesh of at least two sets of helicoidal filaments turning respectively in opposite directions and being intertwined, and wherein the at least two sets of helicoidal filaments of the mesh extend continuously through two distinct tubular sections, a first section and a second section, the second section being comprised of two sub-sections, a first sub-section having a shape with a progressive reduction of diameter configured to open and create a space for the thrombus, and a second sub-section of a tubular uniform diameter configured to provide a connection to a catheter or to a hypotube;

wherein the at least two sets of helicoidal filaments form closed loops at a distal end of the first section;

wherein said mesh of the at least two sets of helicoidal filaments in the first section extends distally with a constant braiding angle from a proximal end of the first section to and around the closed loops back to the proximal end of the first section and is configured to provide outward radial forces higher than in the second section, such that the first section becomes appositioned against the inner wall of the blood vessel in an open position;

wherein:

the closed loops are configured to act as a spring, such that the outward radial forces in first and second end portions of the first section are higher than in an intermediate portion thereof; and said mesh of the first sub-section of the second section has a conical shape and comprises a braiding angle that changes at its proximal and distal ends to provide outward radial strength to maintain the conical shape and to maintain the open position of the first section.

2. The device of claim 1, wherein the segment further comprises a coating covering at least the first section.

3. The device of claim 1, wherein the at least two sets of helicoidal filaments of the mesh are made of a metal, a metal alloy or a composite including Nitinol or Nitinol/Platinum.

4. The device of claim 1, wherein:

the at least two sets of helicoidal filaments comprise a number ranging between 24 and 48, said at least two sets of helicoidal filaments having a cross section comprised in a range between 40 and 60 μm; and the braiding angle of the at least two sets of helicoidal filaments with regard to a longitudinal axis of the segment is comprised between 50 and 65 degrees for the first section, and between 15 and 50 for the second sub-section.

5. The device of claim 1, wherein:

the first section comprises a length ranging between 4 and 40 millimeters and the second sub-section comprises a length ranging between 1 and 10 millimeters; and the first section comprises an outer diameter ranging between 3.5 and 6 millimeters and the second sub-section comprises an outer diameter ranging between 1 and 2 millimeters.

6. The device of claim 1, wherein the braiding angle of the first sub-section is comprised between 15 and 45 degrees with regard to a longitudinal axis of the segment.

7. The device of claim 1, wherein the segment further comprises one or more sensors included or attached thereto to provide information thereof including information on whether the thrombus is in or out, about the composition of the thrombus, about the position of the segment in relation to the blood vessel, on whether the segment is in the retracted position or in the extended and expanded position, on whether the segment is well extended, or about the radial forces.

8. The device of claim 1, wherein the segment further comprises a coating covering at least the first sub-section of the second section.

9. The device of claim 8, wherein the coating is a non-permeable coating.

10. The device of claim 8, wherein the coating comprises holes.

11. The device of claim 8, wherein the coating comprises a polymer including silicone or polyurethane.

12. The device of claim 8, wherein at least a proximal portion of the second sub-section is uncoated.

13. A thrombectomy apparatus including the segment for extraction of thrombus from a blood vessel, according to claim 1.

14. A system configured for automated maneuvering of the thrombectomy apparatus of claim 13 to the blood vessel, the system comprising an automated proximal device configured to provide a guidance system to deploy the thrombectomy apparatus, an imaging device, a communications channel, a control module configured to allow for guidance of the deployment of the thrombectomy apparatus, a data storage device, and a computer assisted controller configured to guide the control module.

* * * * *